US006169217B1

(12) United States Patent
Cheryan

(10) Patent No.: US 6,169,217 B1
(45) Date of Patent: Jan. 2, 2001

(54) METHOD FOR EXTRACTING XANTHOPHYLLS FROM CORN

(75) Inventor: Munir Cheryan, Urbana, IL (US)

(73) Assignee: Board of Trustees of the University of Illinois, Urbana, IL (US)

( * ) Notice: Under 35 U.S.C. 154(b), the term of this patent shall be extended for 0 days.

(21) Appl. No.: 09/421,303

(22) Filed: Oct. 20, 1999

(51) Int. Cl.$^7$ ................................................. C07C 35/21
(52) U.S. Cl. ........................................................ 568/816
(58) Field of Search ............................................ 568/816

(56) References Cited

U.S. PATENT DOCUMENTS

| | | | |
|---|---|---|---|
| 3,069,443 | * 12/1962 | Witte | 568/816 |
| 3,523,138 | * 8/1970 | Grant | 568/816 |
| 4,851,339 | * 7/1989 | Hills | 568/816 |
| 5,382,714 | 1/1995 | Khachik . | |
| 5,602,286 | 2/1997 | Muralidhara . | |
| 5,648,564 | 7/1997 | Ausich et al. . | |
| 5,747,544 | 5/1998 | Garnett et al. . | |
| 5,847,238 | 12/1998 | Muralidhara et al. . | |
| 5,876,782 | 3/1999 | Sas et al. . | |
| 5,998,678 | * 12/1999 | Virgili | 568/816 |

OTHER PUBLICATIONS

B.P. Chew, M.W. Wong, T.S. Wong, "Effects of Lutein from Marigold Extract on Immunity and Growth of Mammary Tumors in Mice", *Anticancer Research*, vol. 16, 1996, pp. 3689–3694.

G. Garelik, "What You Eat May Help Prevent Blindness", *Investor's Business Daily*, Feb. 16, 1999.

W. Boyd, "Ingredients Update: What's New with Natural Colorants", *Cereal Foods World*, vol. 43, No. 9, Sep. 1998, pp. 720–722.

H. Nishino, "Cancer Prevention by Natural Carotenoids", *Journal of Cellular Biochemistry Supplement*, vol. 27, 1997, pp. 86–91.

J.M. Seddon, U.A. Ajani, R.D. Sperduto, R. Hiller, N. Blair, T.C. Burton, M.D. Farber, E.S. Gragoudas, J. Haller, D.T. Miller, L.A. Yannuzzi, W. Willett, "Dietary Caretenoids, Vitamins A, C and E, and Advanced Age–Related Macular Degeneration", *JAMA*, vol. 272, No. 18, Nov. 9, 1994, pp. 1413–1420.

F. Khachik, F.B. Askin, K. Lai, "Distribution, Bioavailability, and Metabolism of Carotenoids in Humans", *Phytochemicals*, Technomic Publishing Co., 1998, pp. 77–95.

K. Broihier, "A Look at Lutein", *Food Processing*, Oct. 1999, pp. 92–93.

"Lutein Plus" Life Extension Foundation web page, (2000).

A. Underwood, "A Prescriptive Palette", *Newsweek*, Dec. 6, 1999, pp. 91–92.

* cited by examiner

Primary Examiner—Michael L. Shippen
(74) Attorney, Agent, or Firm—Greer, Burns & Crain, Ltd.

(57) ABSTRACT

The method of the invention uses raw corn, or a corn by-product as a source. The source is mixed with an alcohol to produce an alcohol-corn slurry. Centrifugation or filtration produces a clear filtrate from the alcohol-corn slurry. A membrane filtration step is then used to separate purified xanthophylls. Other steps may be combined with the basic process to produce additional corn products, such as oil and zein.

10 Claims, 1 Drawing Sheet

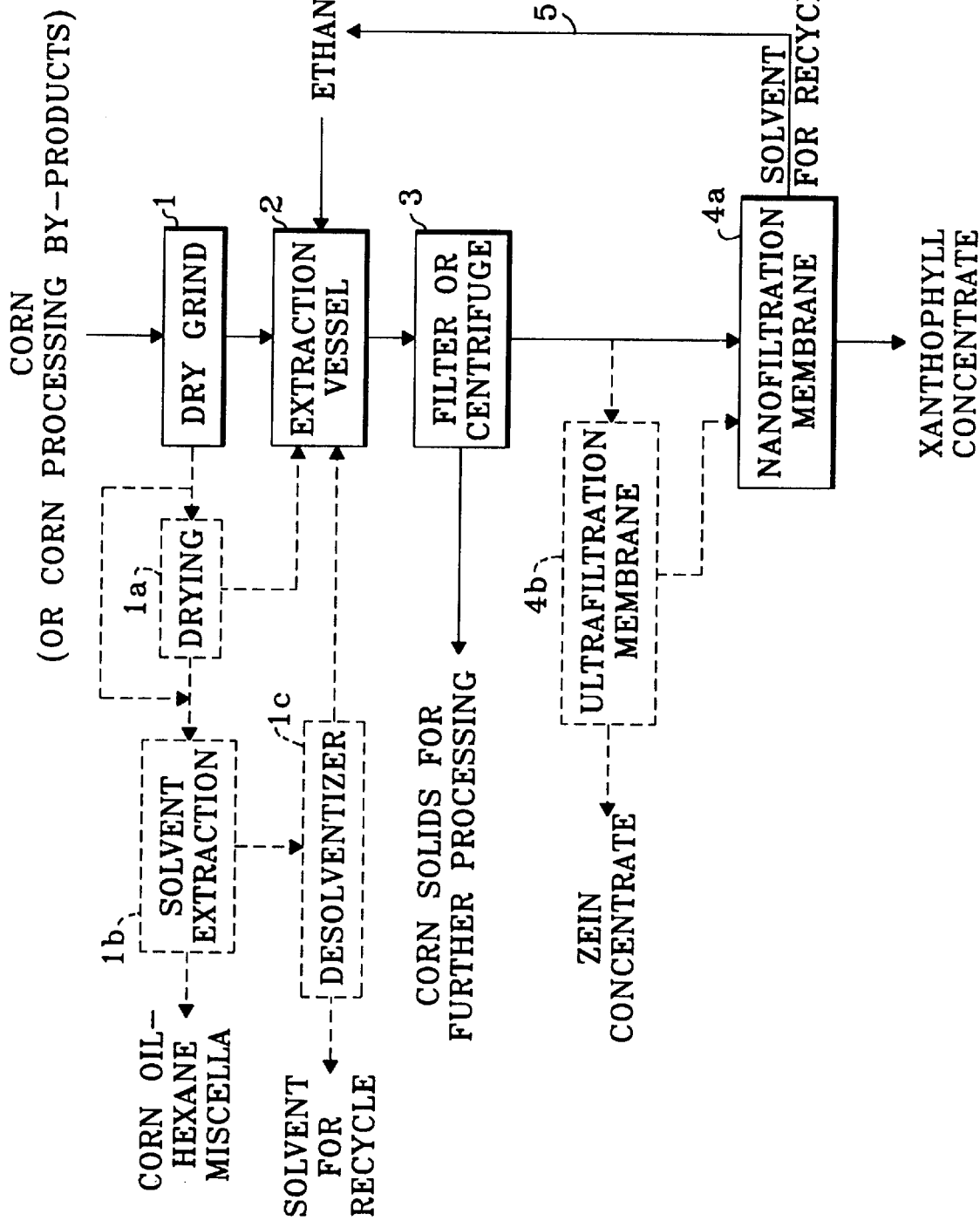

METHOD FOR EXTRACTING XANTHOPHYLLS FROM CORN

The invention generally concerns extraction of xanthophylls. The invention more specifically concerns a method for extraction xanthophylls from various forms of corn, including raw corn as well as corn processing derived co-products.

BACKGROUND OF THE INVENTION

Xanthophylls are oxygenated cartenoid compounds that are useful as yellow pigments that can be used in animal feeds and human food. Various plants and some animal products, e.g. egg yolks, are a source of xanthophylls. Corn gluten is often fed to chickens to impart a yellow color to the chickens which is preferred by consumers of chicken, especially those in the US market. Major producers of chicken have even been known to advertise the yellow hue of their chicken. The method of feeding corn gluten serves this purpose. It is preferable, though, to use extracted xanthophylls to produce consistent results.

Prior art methods have extracted xanthophylls from marigolds. One such method is described in U.S. Pat. No. 5,382,714 to Khachik. The specific xanthophyll, lutein, is extracted from saponified marigold oleoresin.

Extracted lutein is used currently in the health food market, and typically sold as a gel capsule. Some studies have linked lutein, and another xanthophyll, zeaxanthin, to prevention of age-related macular degeneration (AMD), a disorder that can cause blindness in humans. According to a 1994 study by Seddon et al. at Harvard University, the human body absorbs lutein and zeaxanthin from food directly into the human plasma and deposit in the macular and retina of the eyes. The body even metabolically transforms lutein into zeaxanthothin to be deposited in the macular region. The lutein extracted from marigolds has not, however, been approved by the FDA as a food additive. Marigolds, unlike corn, are not on the Generally Recognized As Safe (GRAS) list of the FDA. There have therefore been efforts to produce xanthophylls from products that are on the GRAS list.

U.S. Pat. No. 5,602,286 to Muralidhara describes a method for producing xanthophylls from corn gluten meal. Corn gluten meal is a product of corn wet milling. The process requires a saponification reaction. Its application is limited because of its requirement for wet milling as a precursor to produce the corn gluten required for the process.

Thus, there is a need for an improved method for producing xanthophylls from corn. That need is met or exceeded by the method of the present invention, which permits extraction of xanthophylls from raw corn as well as corn co-products such as corn gluten meal.

SUMMARY OF THE INVENTION

The method of the invention uses raw corn, or a corn by-product as a source. The source is mixed with an alcohol to produce an alcohol-corn slurry. Centrifugation or filtration produces a clear filtrate from the alcohol-corn slurry. A membrane filtration step is then used to separate purified xanthophylls.

BRIEF DESCRIPTION OF THE DRAWING

Other objects, features and advantages of the invention will be apparent by reference to the drawing FIGURE. The FIGURE is a block diagram illustrating the method of the invention.

DETAILED DESCRIPTION OF THE INVENTION

Referring now to the FIGURE, the method of the invention is capable of using raw corn of any form, or corn processing products, such as corn gluten meal produced in wet milling processes. A preliminary dry grind step 1 is required if the corn source is raw corn. In the case of corn processing products, or raw corn which, after grinding, is excessively moist a drying step 1a should be conducted to facilitate a reaction extraction step 2.

The extraction step 2 is conducted with an alcohol of concentration ranging from about 40% to 100%. The preferred alcohol diluent is water. The reaction in the extraction step 2 becomes efficient above approximately 70% alcohol, and alcohol concentrations at or above approximately 92% are preferred if an oil based xanthophyll is preferred. The particular range of alcohol chosen may depend upon whether other products such as corn oil or zein are desired to be obtained. Methods for extraction of oil and zein, and the associated preferred alcohol concentrations during extraction where oil or zein are desired, are fully explained in commonly owned co-pending application Ser. No. 09/313,690, entitled CORN OIL AND PROTEIN EXTRACTION METHOD, which is incorporated by reference herein.

Either batch extraction or continuous extraction is suitable. The continuous extraction can be in a column or commercial co-current or countercurrent extractor such as those manufactured by Crown or Lurgi-PSI for use in the vegetable oil industry. The preferred type of alcohol is ethanol However, other alcohols, e.g., isopropanol, can be used in the extraction step. Temperatures between about 5° C. and 75° C. are suitable, and the extraction reaction should be allowed sufficient time to complete, typically 15 to 120 minutes. The result of the extraction step 2 is a alcohol-corn slurry.

The alcohol-corn slurry is then subjected to filtration or centrifugation (step 3) to remove corn solids. This step may not be required depending upon whether the method of extraction used in step 2 also removes solids. Typical commercial extractors remove solids such that the filtration or centrifugation step 3 would not be required. The objective of filtration or centrifugation is to remove large or suspended particles and produce a clear filtrate containing the xanthophylls in the corn-alcohol slurry from the extraction step 2.

The clear filtrate from step 3, or step 2 if the extraction removes large particles, is then subjected to membrane nanofiltration step 4a. The nanofiltration step 4a is conducted with a membrane pore size designed to retain the xanthophyll molecules, i.e. about a 200–600 molecular weight cut off. Xanthophyll concentrate results from the nanofiltration step 4a. The alcohol passing through the nanofiltration membrane may be recycled (step 5) back for use in further extraction in extraction step 2.

The basic process of the invention is complete with the extraction of xanthophyll concentrate in step 4a. Alternative features of the invention, which extend the process to permit extraction of additional corn products in the same basic process flow of the xanthophyll extraction will now be described. These features, like optional features discussed previously, are shown in dotted lines in the FIGURE.

Solvent extraction, step 1b, is optionally conducted to separate oils from the corn source prior to the reaction in the extraction step 2. As an example, hexane extraction produces a corn oil-hexane miscella. Another exemplary solvent is isopropanol. Generally, any oil extracting solvent is suitable. The miscella may then be sent to an evaporator to remove the hexane, or preferably, through a nanofiltration membrane to concentrate the oil. The nanofiltration method provides a low energy way to permit recycling the hexane back into the hexane extraction step 1b. Residual hexane is removed by a desolventizing step 1c prior to the extraction step 2. Zein concentrate may also be produced through an ultrafiltration step 4b, conducted prior to the nanofiltration step 4a. Corn solids from the separation step 3 can also be used for further conventional processes, such as to produce DDGS or additional ethanol.

While various embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

What is claimed is:

1. A method for extracting xanthophyll from corn, the method comprising steps of:

reacting a source of corn with alcohol to produce an alcohol-corn slurry;

separating solids from the alcohol-corn slurry to produce a clear filtrate;

membrane filtering the clear filtrate to separate xanthophyll concentrate from the clear filtrate.

2. The method according to claim 1, wherein said step of separating comprises centrifugation.

3. The method according to claim 1, wherein said step of separating comprises filtration.

4. The method according to claim 1, wherein said source of corn comprises raw corn.

5. The method according to claim 1, wherein said source of corn comprises a corn processing derived co-product.

6. The method according to claim 1, further comprising a step of drying the source of corn prior to said step of separating.

7. The method according to claim 1, wherein said step of reacting mixes alcohol having a concentration of above approximately 92% with said source of corn.

8. The method according to claim 1, further comprising a step of solvent extraction prior to said step of reacting to remove oils from the source of corn and a step of desolventization to remove excess hexane prior to said step of reacting.

9. The method according to claim 1, further comprising a step of zein filtration, prior to said step of membrane filtrating to remove zein from the clear filtrate and obtain a zein concentrate.

10. The method according to claim 9, wherein said step of zein filtration comprises ultrafiltration.

* * * * *